(12) United States Patent
Adams et al.

(10) Patent No.: US 9,968,433 B2
(45) Date of Patent: May 15, 2018

(54) EMBOLIC PROTECTION PASS THROUGH TUBE

(71) Applicant: St. Jude Medical, Cardiology Division, Inc., St. Paul, MN (US)

(72) Inventors: Daniel Adams, Long Lake, MN (US); Mathias Charles Glimsdale, St. Michael, MN (US); Brian Joseph Perszyk, Brooklyn Park, MN (US); Chris Quinn, Minneapolis, MN (US); Brooke Ren, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days. days.

(21) Appl. No.: 13/782,755

(22) Filed: Mar. 1, 2013

(65) Prior Publication Data

US 2014/0249568 A1 Sep. 4, 2014

(51) Int. Cl.
*A61F 2/01* (2006.01)

(52) U.S. Cl.
CPC ........ *A61F 2/013* (2013.01); *A61F 2002/018* (2013.01); *A61F 2230/0006* (2013.01); *A61F 2230/008* (2013.01); *A61F 2230/0069* (2013.01)

(58) Field of Classification Search
CPC .......... A61F 2002/018; A61F 2002/016; A61F 2002/011; A61F 2/13; A61F 2/01; A61F 2/86; A61F 2/90; A61F 2/91; A61F 2210/0014; A61F 2/00; A61F 2/013; A61F 2002/015; A61F 2230/0006; A61F 6/225; A61B 2230/006; A61B 2230/0069; A61B 2230/008; A61B 2230/001; A61B 5/6858; A61B 1/00085; A61B 17/221; A61B 2017/2212; A61B 2017/2215;
(Continued)

(56) References Cited

U.S. PATENT DOCUMENTS 5,279,573 A 1/1994 Klosterman
5,527,337 A 6/1996 Stack et al.
5,800,457 A 9/1998 Gelbfish
(Continued)

FOREIGN PATENT DOCUMENTS

WO 0053119 A1 9/2000
WO 2006131930 A2 12/2006
(Continued)

OTHER PUBLICATIONS

U.S. Appl. No. 13/782,703, filed Mar. 1, 2013.
(Continued)

*Primary Examiner* — Darwin Erezo
*Assistant Examiner* — Katherine Schwiker
(74) *Attorney, Agent, or Firm* — Lerner, David, Littenberg, Krumholz & Mentlik, LLP

(57) ABSTRACT

An embolic protection device includes an outer surface that is configured to form a substantially sealed relationship with a body lumen such that emboli are deflected and/or captured by the outer surface before such emboli can travel to other parts of the body. An inner surface of the embolic protection device includes a longitudinally extending lumen through which instrumentation may be inserted, facilitating passage of such instrumentation through the body lumen while minimizing risk to the patient from emboli.

11 Claims, 11 Drawing Sheets

(58) Field of Classification Search
CPC ........ A61B 17/12168; A61B 17/12172; A61B 17/12177; A61B 17/12109
USPC ........................................................ 606/200
See application file for complete search history.

(56) References Cited

U.S. PATENT DOCUMENTS

| | | | |
|---|---|---|---|
| 5,800,525 | A | 9/1998 | Bachinski et al. |
| 5,906,641 | A * | 5/1999 | Thompson ................ A61F 2/07 606/191 |
| 6,361,545 | B1 * | 3/2002 | Macoviak ........ A61B 17/12136 606/151 |
| 6,540,767 | B1 | 4/2003 | Walak et al. |
| 2001/0044634 | A1 | 11/2001 | Don Michael et al. |
| 2003/0004539 | A1 | 1/2003 | Linder et al. |
| 2004/0215167 | A1 | 10/2004 | Belson |
| 2006/0100662 | A1 | 5/2006 | Daniel et al. |
| 2006/0161241 | A1 | 7/2006 | Barbut et al. |
| 2006/0229658 | A1 | 10/2006 | Stivland |
| 2006/0293706 | A1 * | 12/2006 | Shimon ......................... 606/200 |
| 2009/0187210 | A1 * | 7/2009 | Mackiewicz ................ 606/200 |
| 2009/0254172 | A1 | 10/2009 | Grewe |
| 2009/0326575 | A1 | 12/2009 | Galdonik et al. |
| 2010/0312268 | A1 * | 12/2010 | Belson ...................... A61F 2/01 606/200 |
| 2011/0190863 | A1 * | 8/2011 | Ostroot ................... A61F 2/013 623/1.11 |
| 2011/0282379 | A1 | 11/2011 | Lee et al. |
| 2012/0172920 | A1 | 7/2012 | Fifer et al. |
| 2012/0179033 | A1 | 7/2012 | Merhi |
| 2013/0046330 | A1 * | 2/2013 | McIntosh ................ A61F 2/013 606/200 |
| 2014/0172006 | A1 | 6/2014 | Stack et al. |
| 2014/0180329 | A1 | 6/2014 | Krahbichler |

FOREIGN PATENT DOCUMENTS

| | | |
|---|---|---|
| WO | 2008066881 A1 | 6/2008 |
| WO | 2008073964 A2 | 6/2008 |
| WO | 2013074521 A1 | 5/2013 |
| WO | 2013134194 A1 | 9/2013 |

OTHER PUBLICATIONS

U.S. Appl. No. 13/782,677, filed Mar. 1, 2013.
U.S. Appl. No. 13/782,657, filed Mar. 1, 2013.
International Search Report for Application No. PCT/US2013/078301 dated Mar. 28, 2014.

* cited by examiner

EMBOLIC PROTECTION PASS THROUGH TUBE

BACKGROUND OF THE INVENTION

The present disclosure generally relates to devices and systems for use within blood vessels, and more particularly to devices and systems for use within blood vessels that deflect and/or trap emboli.

Arterial embolism is a sudden interruption of blood flow to an organ or body part due to an embolus, e.g., debris or a clot. During a medical procedure, thrombi may form and emboli may move, dislodge or break free within arteries. As used herein, the term emboli refers generally to any particles or debris moving within the bloodstream. These emboli are capable of traveling far from their origins, migrating to other sites of the vasculature where they may obstruct the flow of blood. For example, an embolus may travel through the carotid artery and inhibit the flow of blood to the brain, which may result in the death of brain cells, i.e., cause a stroke. Blockage of the carotid arteries is the most common cause of a stroke.

BRIEF SUMMARY OF THE INVENTION

Disclosed herein are embolic protection devices which facilitate passage of instrumentation through a patient's vasculature while minimizing the risk from emboli traveling within a patient's vasculature.

In an embodiment, an embolic protection device may include a tubular sheet having a first end and a second end, and a delivery catheter. The first end of the tubular sheet may be fixedly connected to the delivery catheter, and the second end of the tubular sheet may be translatable through the delivery catheter.

In another embodiment, an embolic protection may have a proximal section, a distal section, and an intermediate section between the proximal and distal sections. The intermediate section may have a first diameter, and the proximal and distal sections may each have a diameter that is greater than the first diameter. The elongated tubular body may be transitionable between an unfolded configuration in which the intermediate section is positioned between the proximal and distal sections, and a folded configuration in which the distal section is inverted over the intermediate section.

In yet another embodiment, an embolic protection device may include a tube formed from a compressible material, and may have a first end, a second end, and a diameter. A wire may operatively couple the first end and the second end of the tube. The wire may be translatable relative to the tube to cause a corresponding movement of the first end of the tube relative to the second end of the tube and a corresponding change in the diameter of the tube.

In a still further embodiment, an embolic protection device may include a tube that is transitionable between a compressed condition and an expanded condition. The first section may have a first diameter. The second section may have a second diameter that is smaller than the first diameter. The first section may include a first lumen through which the second section is translatable. The second section may include a second lumen through which an elongated instrument is insertable.

In a still further embodiment, an embolic protection device may include a tubular member having an outer layer and an inner layer. The inner layer may have a first section with a first diameter, a second section with a second diameter, and an intermediate section with a diameter smaller than the diameters of the first and second sections and positioned between the first and second sections. A lumen may extend continuously through the first section, the second section, and the intermediate section. The lumen may be configured to receive an elongated instrument therethrough.

In yet another embodiment, an embolic protection device may include an elongated tubular body having a longitudinal axis, a first section, a second section, and a third section. The body may be configured to transition between an expanded state and a compressed state, and may be biased toward the expanded state. The second section may be dispoised between the first section and the third section. The second section may be relatively narrower than the first section and the third section in the expanded state. A lumen may extend through the body along the longitudinal axis. The lumen may be sized to receive an elongated instrument therethrough. The elongated instrument may be radially spaced from the outer surfaces of the first and third sections when the instrument is positioned within the lumen.

These and other embodiments of the present disclosure are more fully described hereinbelow.

BRIEF DESCRIPTION OF THE DRAWINGS

Embodiments of the present disclosure are described with reference to the accompanying drawings, in which.

DETAILED DESCRIPTION

Figure 1:
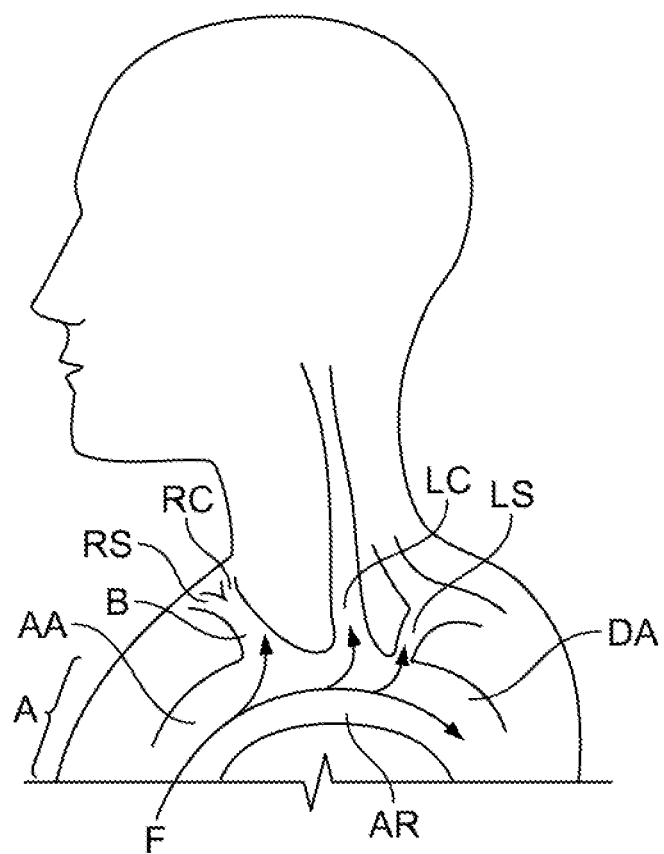
FIG. 1 is a diagrammatic view of a portion of a patient's vascular system.

Particular embodiments of the present disclosure are described with reference to the accompanying drawings. In the figures and in the description that follow, like reference numerals identify similar or identical elements. As used throughout the following description, the term "proximal" refers to the end or portion of a device that is relatively close to the user deploying the device, and the term "distal" refers to the end or portion of the device that is relatively farther away from the user deploying the device. As used herein, the term "tube" may refer to any elongated body through which an instrument may be passed, and is not limited to any particular geometric shape, and may be for example, cylindrical or conical in shape.

The aorta is the main trunk of a series of vessels that convey oxygenated blood to the tissues of the body. As shown in FIG. 1, aorta A includes ascending aorta AA, which commences at the upper part of the left ventricle of the heart. After ascending for a short distance, aorta A arches backward and to the left side to form aortic arch AR, which transitions to descending aorta DA, which descends within the thorax. Aortic arch AR commonly includes three arterial branches: brachiocephalic artery B, left common carotid artery LC, and left subclavian artery LS. Brachiocephalic artery B supplies blood to the right arm, the head, and the neck. Typically, brachiocephalic artery B includes a common brachiocephalic trunk, which branches into right subclavian artery RS and right common carotid artery RC. Left common carotid artery LC branches into internal and external vessels near the top of the thyroid, and supplies blood to the brain and other tissues within the skull. Left subclavian artery LS supplies blood to the left arm, with some branches supplying blood to the head and thorax. It is to be understood that the anatomy of a particular individual may differ, and that the description of particular anatomical features is merely illustrative and should not be construed as limiting the disclosure.

A thrombus or blood clot may form within an artery, when blood flow is sluggish, enabling clotting factors to accumulate and giving platelets an opportunity to stick together. An embolus is most often a piece of a thrombus that has broken free. However, an embolus may also be plaque, fat, and other material. An embolus travels with the flowing blood until it reaches a narrowing in the artery through which it cannot pass, blocking the artery. During a vascular procedure, such as a transcatheter aortic valve implantation (TAVI) procedure (also known as transcatheter aortic valve replacement (TAVR) procedure), emboli may be dislodged as surgical instrumentation passes through the vasculature, and, for example, causes plaque to become dislodged or scrapes tissue from the artery during the translation of the instrumentation.

Figure 2A:
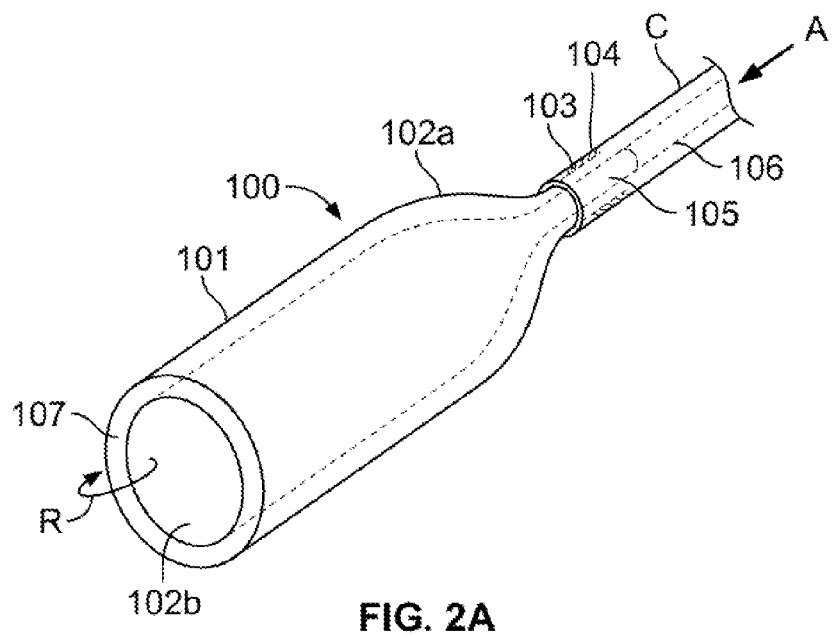
FIG. 2A is a perspective view of an embodiment of an embolic protection device being deployed from a catheter.
Figure 2B:
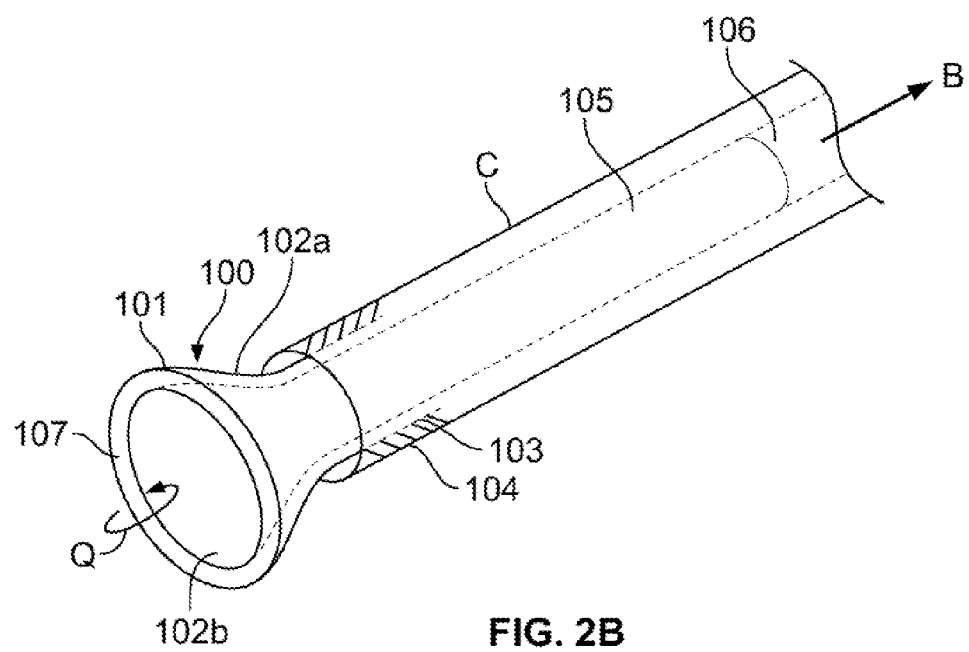
FIG. 2B is perspective view of the embolic protection device of FIG. 2A partially deployed from the delivery catheter.

Various embodiments of devices and systems for deflecting and/or capturing emboli are described with reference to FIGS. 2A-15. Embolic protection device 100 is shown in FIGS. 2A and 2B. Device 100 includes a tubular sheet 101 that may be formed from a braided or mesh-like material. The material may have shape memory properties, such as exhibited by a nickel titanium alloy, and may be transitionable between a compressed state and an expanded state. Tubular sheet 101 has outer surface 102a and inner surface 102b, one or both of which may be coated with a substance having anti-thrombogenic properties, such as heparin. Tubular sheet 101 has a fixed end 103 that is secured at or near the distal end 104 of a delivery catheter C, and a free end 105 that is translatable through delivery catheter C. Free end 105 of tubular sheet 101 may be operatively coupled to delivery tube 106, which is translatable through delivery catheter C, so that movement of delivery tube 106 may cause a corresponding movement of free end 105 of tubular sheet 101. Instrumentation for performing a surgical procedure may be passed through delivery tube 106, as well as through tubular sheet 101. The length of tubular sheet 101 extending from distal end 104 of delivery catheter C is adjustable by translating free end 105 of tubular sheet 101 relative to delivery catheter C. Tubular sheet 101 will be folded upon itself when deployed such that, when deployed, distal end 107 of the tubular sheet will be a folded edge. Tubular sheet 101 may have a heat-set crease preformed at a spaced distance from its free end 105. In a fully deployed condition, the crease may define distal end 107 of the deployed tube. When any portion of tubular sheet 101 is deployed from delivery catheter C, the width thereof may expand to a width that is greater than the inner diameter of the delivery catheter.

Device 100 may be deployed within a patient's vasculature using catheter-based techniques to achieve desired placement. The delivery of device 100 may occur via a transfemoral approach (through the inguinal crease), a transradial approach (through an artery in the arm), or any other percutaneous approach. For example, in a transfemoral approach, delivery catheter C may be maneuvered up through aortic arch AR, and once it is in a desired position, delivery tube 106 may be pushed through the delivery catheter to cause a corresponding translation of free end 105 of tubular sheet 101 in direction A along the delivery catheter. As free end 105 of tubular sheet 101 is distally translated, tubular sheet 101 will evert as distal end 107 thereof rolls in direction R and the length of the tubular sheet extending from distal end 104 of delivery catheter C becomes greater. Tubular sheet 101 may be deployed to its fully expanded condition in which the crease is at distal end 107 of the deployed tubular sheet or may be deployed by some lesser amount. Advantageously, the rolling motion of distal end 107 of tubular sheet 101 during deployment of the tubular sheet minimizes the generation of emboli. As tubular sheet 101 is deployed from delivery catheter C, it automatically transitions to its expanded state (FIG. 2A) in which outer surface 102a of the tubular sheet engages the wall of aortic arch AR in apposition to one or more of arterial branches B, LC, and/or LS (not shown). The curvature of tubular sheet 101 in the expanded state may correspond to the natural curvature of the aorta, such that the deployed tube fills the cross-section of the aorta. Tubular sheet 101 is positionable in aortic arch AR (FIG. 1) such that emboli present in the blood flowing through the aortic arch may flow into the interior of the deployed tubular sheet, and are blocked from entering one or more of arterial branches B, LC, and/or LS (FIG. 1). Furthermore, emboli within the flowing blood may be directed through tubular sheet 101 and into delivery tube 106, thereby capturing such emboli.

A surgical instrument, such as a valve delivery catheter, may be inserted through delivery tube 106 and through the interior of tubular sheet 101. After completion of a desired surgical procedure, delivery tube 106 may be pulled farther into delivery catheter C to cause a corresponding translation of free end 105 of tubular sheet 101 in direction B into the delivery catheter (shown in FIG. 2B). As a result, distal end 107 of tubular sheet 101 will roll in direction Q as tubular sheet 101 inverts in the opposite direction and the length of tubular sheet 101 extending from distal end 104 of delivery catheter C is decreased. The retraction of tubular sheet 101 may continue until tubular sheet 101 is substantially entirely within delivery catheter C.

Figure 3A:
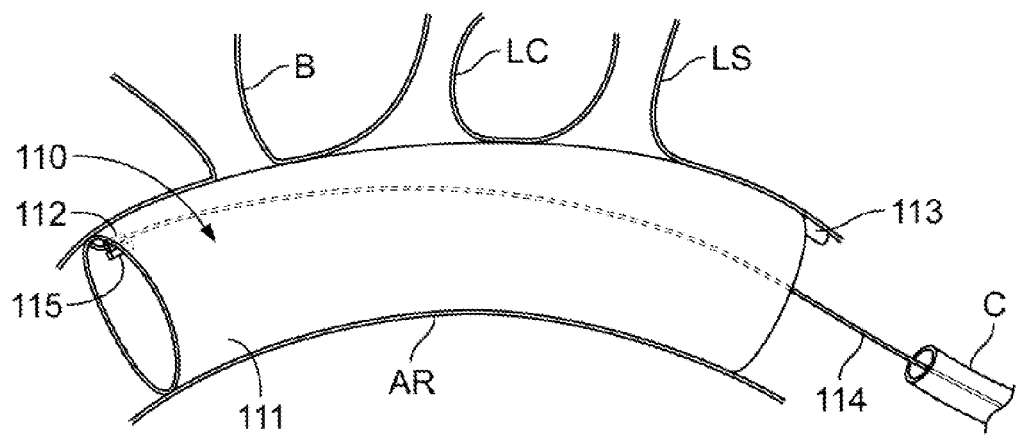
FIG. 3A is a diagrammatic view of another embodiment of an embolic protection device disposed within a patient's vasculature system.
Figure 3B:
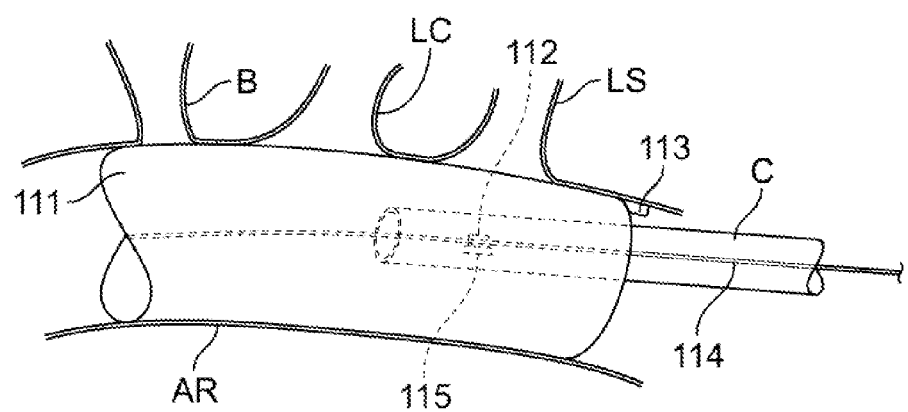
FIG. 3B is a diagrammatic view of the embolic protection device of FIG. 3A in a second condition within the patient's vasculature system.

Another embodiment of an embolic protection device 110 is shown in FIGS. 3A and 3B. Device 110 may include a generally cylindrical tube 111 formed from a braided or mesh-like material or from a porous foam through which blood may flow while emboli of a predetermined size are deflected and/or captured before they can enter branches B, LC, and/or LS of aortic arch AR. The material forming tube 111 may exhibit shape memory properties, such as those exhibited by a nickel titanium alloy or a porous elastic foam, such that the tube is compressible to a smaller size and may be translated through delivery catheter C. As with the previously described embodiments, the components of device 110 may be coated with a substance having anti-thrombogenic properties. The ends of tube 111 may be contained within a distal crimp tube 112 and/or a proximal crimp tube 113. One or more of crimp tube 112 and 113 may be releasably attachable to wire 114, such as via a magnetic connection, a screw connection, a hook and loop type connection or the like. For example, wire 114 may include magnet 115 at a distal end thereof, and may be magnetically coupled to one of the crimp tubes 112 and 113.

Device 110 is deliverable via any percutaneous delivery approach, including a transfemoral delivery approach in which the device is loaded in a compressed condition within delivery catheter C, which is maneuvered within the patient's vasculature toward the aortic arch AR. Deployment of device 110 may be achieved by pushing wire 114, which is operatively coupled to one of distal crimp tube 112 and proximal crimp tube 113, through delivery catheter C. As device 110 device 110 is deployed from delivery catheter C, the device expands to frictionally engage the wall of aortic arch AR such that tube 110 shields one or more of the ostia leading to arterial branches B, LC, and LS. Once device 110 is deployed, wire 114 may be disengaged from the crimp tube 112 or 113 to which it was coupled. Device 110 may remain deployed throughout the primary procedure, such as a TAVI procedure. After completing the primary procedure, device 110 may be retrieved by coupling wire 114 to one of crimp tubes 112 or 113 and drawing the wire into delivery catheter C. For example, wire 114 may be coupled to proximal crimp tube 113 and pulled back into delivery catheter C. Alternatively, wire 114 may be coupled to distal crimp tube 112 such that, as wire 114 is retracted into delivery catheter C, tube 111 is inverted and drawn into the delivery catheter, as illustrated in FIG. 3B. Advantageously, the inversion of tube 111 may facilitate capture and removal of emboli within the tube as it is being retracted into delivery catheter C.

Figure 4:
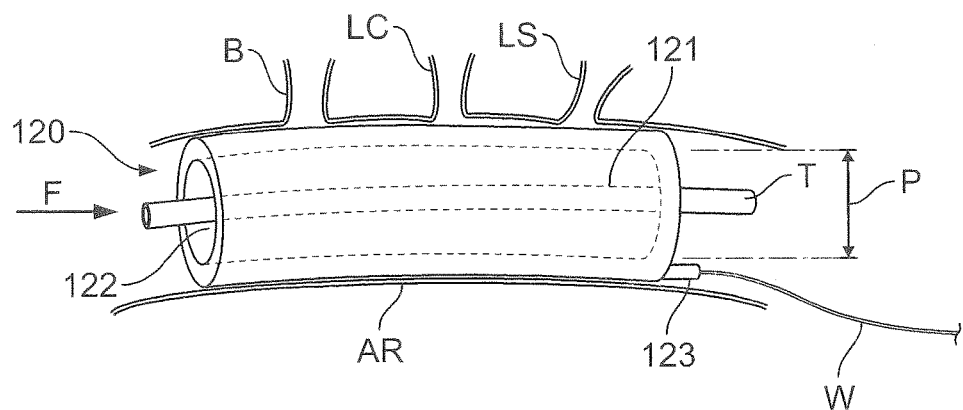
FIG. 4 is a diagrammatic view of a further embodiment of an embolic protection device disposed within a patient's vasculature system.

A still further embodiment of an embolic protection device is shown in FIG. 4. Device 120 includes tube 121 having a generally cylindrical configuration with a lumen 122 extending longitudinally therethrough. Lumen 122 may have a constant diameter P along substantially the entire length of tube 121. Tube 121 may be formed from a braided or mesh-like material or from a porous foam through which blood may flow while emboli greater than a predetermined size are deflected and/or captured before they can enter arterial branches B, LC, and/or LS or aortic arch AR. Crimp tube 123 may be crimped to at least one of proximal end 124 and distal end 125 of tube 121 to crimp the material forming tube 121 therein, and may couple tube 121 to wire W. As with the previously described embodiments, device 120 may be transitionable between a collapsed condition for insertion into a delivery catheter, and an expanded condition, and preferably is formed from a nickel titanium alloy or other shape memory material that may be coated with a substance having anti-thrombogenic properties. Device 120 may be biased toward the expanded condition so that, upon deployment from a delivery catheter, it will automatically expand.

Device 120 may be deployed within a patient's vasculature using catheter-based techniques to achieve desired placement. The delivery of device 120 may occur via a transfemoral approach, a transradial approach, or any other percutaneous approach. Device 120 may be compressed and loaded into the delivery catheter in the compressed condition. When the delivery catheter is positioned in or near aortic arch AR, device 120 may be deployed by pushing wire W through the delivery catheter. In the deployed condition, the distal end of tube 121 is preferably positioned upstream of brachiocephalic artery B so that the tube covers the ostia leading to one or more of arterial branches B, LC, and LS. Once device 120 has been deployed, blood flowing in the direction of arrow F, including during a procedure performed upstream of the device, will flow through lumen 122 of tube 121 and may flow through the wall of tube 121 into arterial branches B, LC, and/or LS. Any emboli that are larger than a predetermined size, however, will be deflected away and therefore, prevented from entering arterial branches B, LC, and/or LS by tube 121. Elongated instruments T are translatable through lumen 122 to facilitate performance of a desired procedure, such as a valve repair procedure. Once the desired procedure has been completed, device 120 may be retrieved by pulling wire W back into the delivery catheter.

Figure 5:
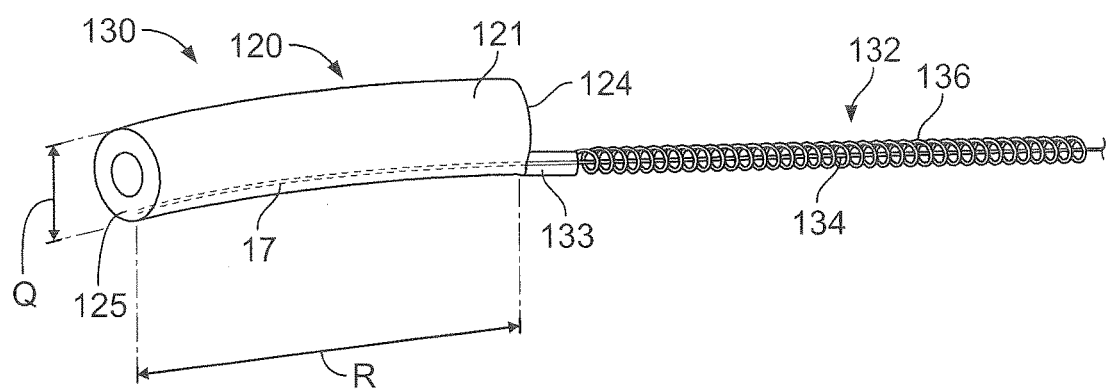
FIG. 5 is a perspective view of an embolic protection system including the embolic protection device of FIG. 4.

In a still further embodiment, as shown in FIG. 5, embolic protection system 130 may include embolic protection device 120 and a stiffening device 132. Stiffening device 132 may include a holder 133 operatively coupled to proximal end 124 of tube 121. Wire 134 may extend through holder 133 and through the length of tube 121, and may be secured to distal end 125 of the tube. Holder 133 may frictionally engage wire 134 to hold the wire in a given position unless a sufficient force is applied to overcome the frictional force. Helical or coiled strand 136 may be disposed around wire 134, and may be operatively coupled to holder 133. Stiffening device 132 is configured to adjust distance R between proximal end 124 and distal end 125 of tube 121 to cause a corresponding adjustment in the outward radial force exerted by tube 121 when it is positioned within aortic arch AR. For example, reducing distance R may result in a corresponding increase in diameter Q of tube 121, causing tube 121 to push against the wall of aortic arch AR with a greater force than when tube 121 is deployed therein without stiffening device 132. Rotation of helical strand 136 may change the pitch of the helix, thereby increasing the rigidity of helical strand 136. An increase in the rigidity of helical strand 136 may facilitate maneuvering and/or stabilizing of tube 121 within the aortic arch. In addition, as the pitch of helical strand 136 is increased, the helical strand may exert a compressive force against the material of tube 121, which may increase the rigidity of tube 121. Moreover, a tensile force may be applied to wire 134, resulting in a reduction of distance R and causing tube 121 to transition toward a larger diameter. By reducing distance R between proximal end 124 and distal end 125, the amount of material per area of the tube is increased, and therefore the rigidity of tube 121 is correspondingly increased. In so doing, the hoop stress, which is the average force exerted circumferentially, of tube 121 may be adjusted as desired.

Figure 6:
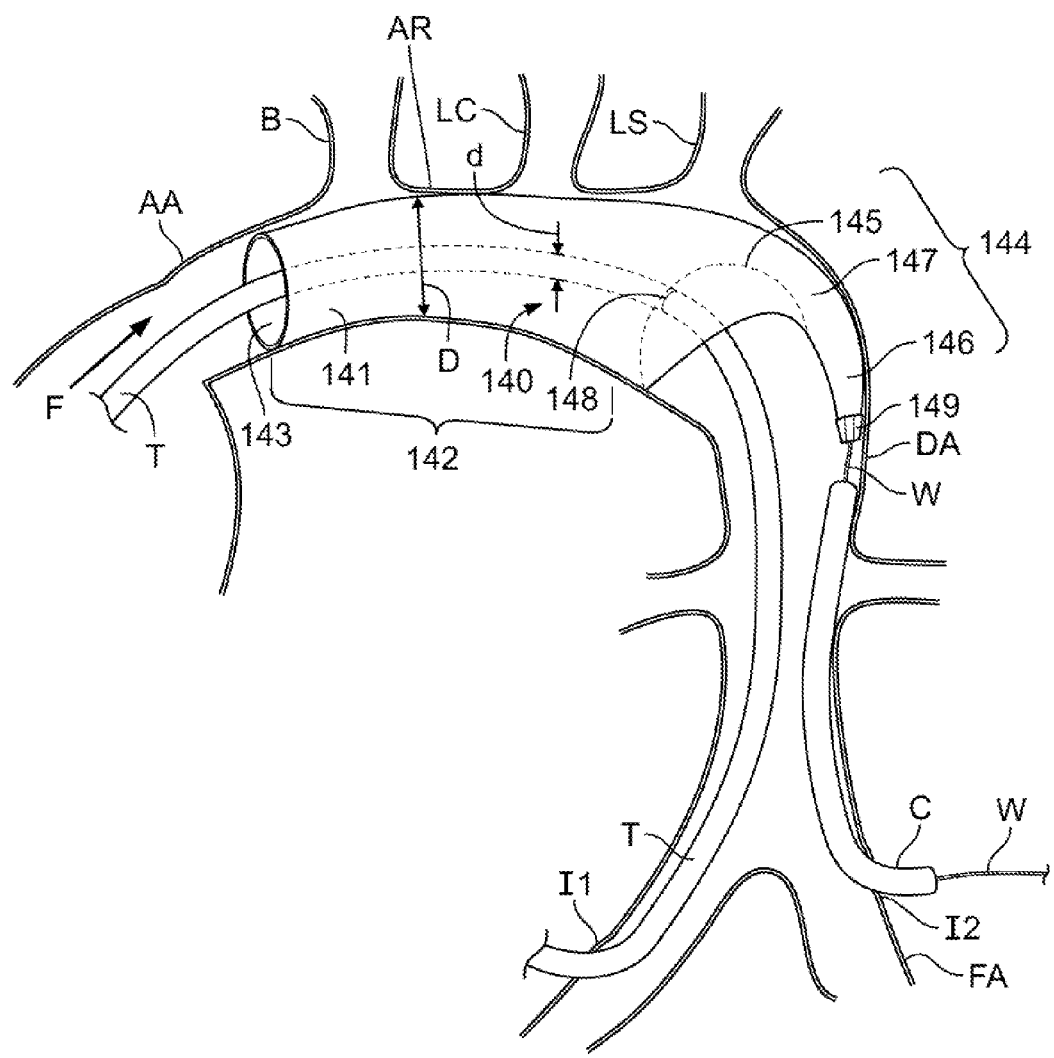
FIG. 6 is a diagrammatic view of another embodiment of an embolic protection device disposed within a patient's vasculature system.

In another embodiment, shown in FIG. 6, embolic protection device 140 includes an elongated generally cylindrical tube 141 that may be formed from a material having shape memory properties, such as those exhibited by a nickel titanium alloy. Tube 141 may be compressible for loading into delivery catheter C, and may be biased toward the expanded state such that, after being compressed, the tube will transition back toward the expanded state. Tube 141 and the other components of device 140 may be coated with a substance having anti-thrombogenic properties. Tube 141 may be formed from a braided or mesh-like material or from a porous foam through which blood may flow while emboli of a predetermined size are deflected and/or captured. First portion 142 of tube 141 includes opening 143, which extends along the length of first portion 142 and has a fully expanded diameter D. Diameter D is larger than the diameter of aortic arch AR so that, when device 140 is deployed in aortic arch AR, first portion 142 will frictionally engage the walls of aortic arch AR. Second portion 144 of tube 141 is joined to first portion 142 and includes inverted portion 145, and emboli collection area 146. Emboli collection area 146 is disposed at the proximal end of tube 141 and includes a narrowed inlet 147. Emboli that may enter tube 141 through opening 143 may pass through tube 141 and be collected or trapped within emboli collection area 146. Inverted portion 145 of tube 141 tapers inwardly toward first portion 142 to opening 148, which has diameter d. Opening 148 is sized to receive elongated instrument T therethrough, such as a valve delivery catheter, which may be introduced into the patient's vascular system via an incision I1. Inverted portion 145 of tube 141 may be generally cone shaped to facilitate insertion of instrumentation through opening 148. Second section 144 may include crimp tube 149, which may inhibit the braided material of tube 141 from unraveling. Crimp tube 149 may be attached to wire W to facilitate the deployment of device 140 from delivery catheter C.

The deployment of embolic protection device 140 may be achieved by loading the device into delivery catheter C in a compressed state, and maneuvering delivery catheter C toward aortic arch AR via a percutaneous access approach. For example, delivery catheter C may be delivered via a transfemoral approach, for example by making an incision 12 and introducing the delivery catheter into femoral artery FA, and maneuvering the delivery catheter toward aortic arch AR. When delivery catheter C reaches a desired position, wire W may be pushed through delivery catheter C, causing device 140 to be deployed from delivery catheter C. As device 140 is deployed, it automatically transitions to its expanded state in which first portion 142 engages the wall of aortic arch AR in apposition to one or more of arterial branches B, LC, and/or LS. Once device 140 has been deployed, any blood flowing in the direction of arrow F, including during a procedure performed upstream of the device, will flow into tube 141 through opening 143 and out through the mesh-like material at second portion 144 of tube 141. For example, during the TAVI procedure, elongated instrument T, such as a delivery catheter, may be inserted through tube 141 to access a target site upstream of tube 141. Elongated instrument T may be received snuggly within opening 148 having a diameter d approximately that of elongated instrument T so that emboli flowing within the blood are inhibited from exiting through opening 148. Any emboli traveling with the blood flow that are larger than the openings in the mesh-like material will be trapped in emboli collection area 146. Once the surgical procedure has been completed, device 140 may be retrieved by proximally translating wire W to pull device 140 back into delivery catheter C. As device 140 is withdrawn into delivery catheter C, it is forced into the compressed condition whereupon delivery catheter C may be removed from the patient.

Figure 7:
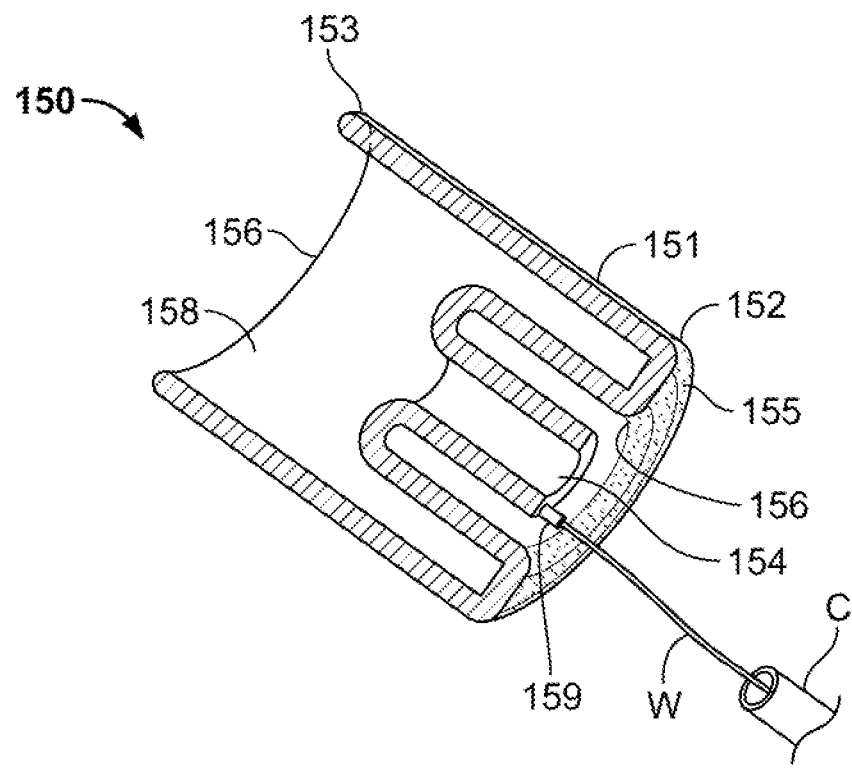
FIG. 7 is a cross-sectional perspective view of a further embodiment of an embolic protection device.

In yet a further embodiment, shown in FIG. 7, embolic protection device 150 may include tube 151 formed from a braided or mesh-like material or from a porous foam through which blood may flow, which tube 151 may capture and/or deflect emboli larger than a predetermined size before they can enter branches B, LC, and/or LS of aortic arch AR when deployed therein. The material forming tube 151 may exhibit shape memory properties, such as those exhibited by a nickel titanium alloy or a porous elastic foam, and tube 151 may be transitionable between a compressed state and an expanded state. Device 150 may be coated by a substance having anti-thrombogenic properties. Tube 151 may be compressible to a smaller size for loading into and translation through delivery catheter C, and may transition to the expanded state upon deployment from delivery catheter C. Tube 151 may have a relatively small diameter for a predetermined length at proximal end 152, a relatively large diameter at distal end 153, and may taper outwardly from the small diameter section to the large diameter section. A portion of tube 151 from proximal end 152 may be folded back and forth upon itself such that the tapered region and a portion of the larger diameter section encircles the smaller diameter section. The smaller diameter section at proximal end 152 has tubular opening 154 configured to receive instrumentation, such as a valve delivery catheter, therethrough. Proximal end 152 of folded tube 151 may include a plurality of small openings 155. Proximal end 152 of folded tube 151 includes a fold 156 configured to permit the flow of blood while minimizing the passage of emboli therethrough. Distal end 153 of tube 151 may have a relatively large opening 156 leading to a hollow interior 158. When positioned within catheter C, tube 151 may be unfolded so that the portion of tube 151 forming tubular opening 154 is positioned external to hollow interior 158 of tube 151, and the diameter of tube 151 may be compressed to fit within the smaller diameter of delivery catheter C. Tube 151 may be biased toward its folded configuration (as shown in FIG. 7) by being, for example, heat set, and may also be biased toward its expanded condition (as shown in FIG. 7) so that tube 151 may automatically assume its expanded and folded configuration upon deployment from delivery catheter C. The depth to which fold 156 is positioned within hollow interior 158 may thus be predetermined and automatically assumed upon deployment of tube 151.

A filter material (not shown), such as a polymer or a polyurethane foam, may be secured, e.g., stitched, to the mesh-like material forming tube 151 to facilitate capture of emboli therein. The filter material may line the interior of tube 151. A crimp tube 159 may crimp the material forming tube 151 at its proximal end 152. Crimp tube 159 may facilitate coupling of device 150 to wire W.

Deployment of device 150 may be achieved in substantially the same manner as described above with respect to the other protection devices. For example, device 150 may be delivered via a transfemoral approach by loading the device into delivery catheter C in a compressed condition, and maneuvering delivery catheter C up through the aortic arch. When delivery catheter C is positioned as desired within the patient's vasculature, wire W may be distally translated through delivery catheter C to push device 150 therefrom. As device 150 is deployed from delivery catheter C, device 150 may automatically expand to its expanded state. Device 150 may be positioned close to ascending aorta AA, upstream with respect to arterial branches B, LC, and/or LS, with proximal end 152 thereof positioned closer to descending aorta DA. In the deployed condition, emboli larger than a predetermined size flowing within the bloodstream into hollow interior 158 will be unable to pass through small openings 155 at proximal end 152 of tube 151. Device 150 may remain deployed within the aortic arch during the course of a primary procedure, such as a TAVI procedure. Instrumentation used for performing the primary procedure may pass through opening 154 and through hollow interior 158 of tube 151.

Once the primary procedure has been completed, device 150 may be retrieved. During retrieval of device 150, wire W may be pulled through delivery catheter C to retrieve and compress tube 151 through delivery catheter C. As tube 151 is retrieved into delivery catheter C, proximal end 152 of tube 151 is compressed within delivery catheter C. Continued pulling of tube 151 into delivery catheter C causes tube 151 to unfold and become compressed within delivery catheter C. During retrieval of tube 151 into delivery catheter C and until tube 151 is substantially retrieved, distal end 153 may remain substantially engaged with the wall of aortic arch AR so that emboli within the blood flowing through aortic arch AR are directed toward proximal end 152 of tube 151 and into delivery catheter C. In so doing, any emboli present in the blood are drawn into and collected within delivery catheter C.

Figure 8:
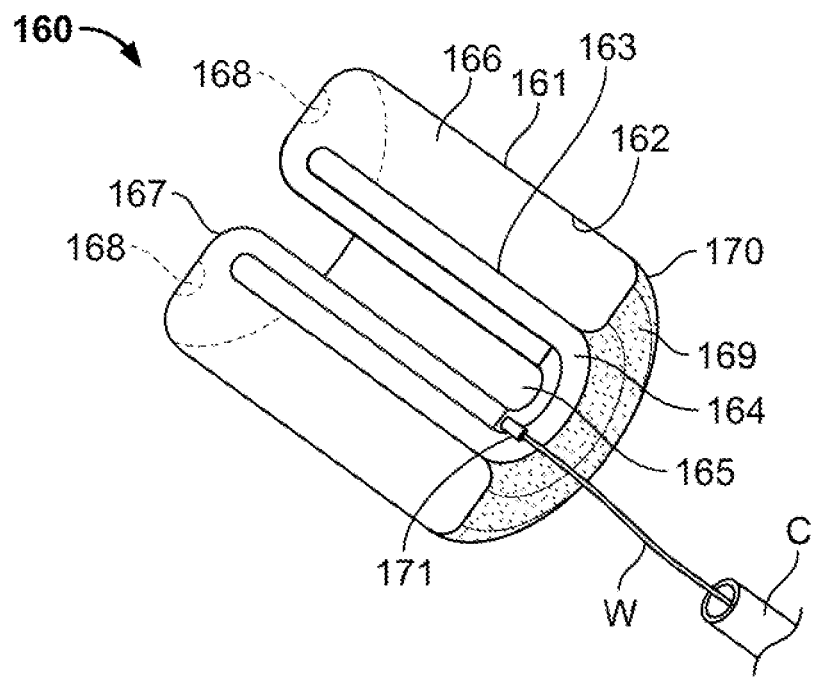
FIG. 8 is a cross-sectional perspective view of another embodiment of an embolic protection device.

Yet another embodiment of embolic protection device 160 is shown in FIG. 8. Device 160 includes tube 161 which may be formed from a braided or mesh-like material or from a porous foam through which blood may flow, which tube 161 may deflect and/or capture emboli larger than a predetermined size before they can enter branches B, LC, and/or LS of aortic arch AR when deployed therein. The material forming tube 161 may exhibit shape memory properties, such as those exhibited by a nickel titanium alloy or a porous elastic foam, and tube 161 may be transitionable between a compressed state and an expanded state. Device 160 may also be coated with a substance having anti-thrombogenic properties.

Tube 161 may be compressible to a smaller size for loading into and translation through a delivery catheter C, and may transition to the expanded state upon deployment from delivery catheter C. Tube 161 may be loaded into delivery catheter C in a compressed condition in an unfolded condition in which the portion of tube 161 defining channel 165 will be retrieved before the remainder of tube 161. Tube 161 may include an outer surface 162 and an inner surface 163. The spacing between outer surface 162 and inner surface 163 may be relatively wider along a first length of tube 161, and relatively narrower along a second length of the tube. The relatively narrower portion of tube 161 may be folded to form fold 164, with the folded portion forming channel 165 that extends substantially along the entire length of tube 161 in this folded configuration. The relatively wider portion of tube 161 may have hollow interior 166 having a generally annular configuration, as shown in FIG. 8. A filter material may line an interior of hollow interior 166 to facilitate capture of emboli that may pass through tube 161. At distal end 167 of tube 161, one or more openings 168 may be formed in the tube and may lead to hollow interior 166. A plurality of openings 169 may be formed at proximal end 170 of tube 161 and lead to hollow interior 166. Openings 168 at distal end 167 of tube 161 may be larger than openings 169 at proximal end 170 of the tube so that emboli within the flowing blood may enter into hollow interior 166 but will be prevented from exiting through the relatively small openings 169. Crimp tube 171 may crimp the material forming tube 161 at proximal end 170 thereof, and wire W may be coupled to crimp tube 171.

Deployment of device 160 may be achieved in substantially the same manner as described above with respect to device 150. For example, device 160 may be loaded into delivery catheter C in an unfolded condition and a compressed condition in which the diameter of the device approximates that of the catheter. Once device 160 is loaded within delivery catheter C, the catheter may be maneuvered up through aortic arch AR.

When delivery catheter C is positioned as desired within the patient's vasculature, wire W may be distally translated through delivery catheter C to push device 160 therefrom. As device 160 is deployed from delivery catheter C, the device may automatically expand to its expanded state. Device 160 may be positioned closer to ascending aorta AA, upstream with respect to arterial branches B, LC, and/or LS, with proximal end 170 thereof positioned closer to descending aorta DA. An instrument may be inserted through channel 165, which may approximate the diameter of the instrument inserted therethrough. When device 160 is deployed, any emboli within the bloodstream will be directed through openings 168 and into hollow interior 166 of tube 161. The relatively small size of openings 169 will prevent emboli larger than a predetermined size from exiting hollow interior 166. Device 160 may remain deployed within the aortic arch during the course of a primary procedure, such as a TAVI procedure. Instrumentation used during the primary procedure may pass through channel 165.

Figure 9:
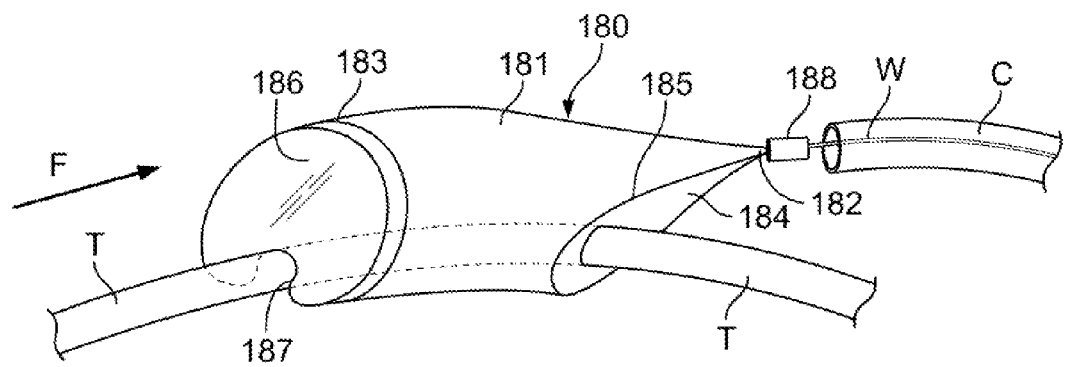
FIG. 9 is a perspective view of a still further embodiment of an embolic protection device.

In a further embodiment, shown in FIG. 9, embolic protection device 180 includes elongated tube 181 having proximal end 182, distal end 183, and hollow interior 184 extending along the length of tube 181. Tube 181 may be formed from the same materials described above with respect to the other embodiments. In particular, tube 181 may be formed from a braided or mesh-like material or from a porous foam through which blood may flow while emboli of a predetermined size are deflected and/or captured before they can enter branches B, LC, and/or LS of aortic arch AR. Tube 181 may be formed from a material having shape memory properties, such as those exhibited by a nickel titanium alloy or a porous elastic foam, so that tube 181 is compressible to a smaller size that enables it to be inserted into and translated through delivery catheter C. As with the other devices described herein, tube 181 and the other components of device 180 may be coated with a substance having anti-thrombogenic properties. Proximal end 182 of tube 181 may include an opening 185 leading to hollow interior 184. Opening 185 may be angled with respect to the longitudinal axis of tube 181. Filter 186 having a disc-like shape may be disposed in and may substantially close distal end 183 of tube 181. Filter 186 may be formed from a polymer, such as a polyurethane foam, from a sufficiently porous fabric material, or from other similar types of materials capable of providing a filtering function. Filter 186 may be transitionable between an expanded condition and a compressed condition so as to be compressible along with the rest of device 180. Opening 187 in filter 186 is sized to snugly receive therethrough instruments T for performing a desired procedure. One such instrument T may be preloaded within device 180 prior to the deployment of device 180 or may be introduced subsequent to the deployment of device 180 so that the instrument passes through opening 185, hollow interior 184, and opening 187 in filter 186. Crimp tube 188 may be crimped to an edge of tube 181 at proximal end 182 to hold the free ends of the material forming tube 181 together. Crimp tube 188 may also couple tube 181 to wire W to facilitate deployment of device 180 into the patient's vasculature.

Deployment of device 180 may be achieved by any suitable percutaneous approach. For example, device 180 may be delivered via a transfemoral approach by loading the device into delivery catheter C in a compressed condition, and maneuvering delivery catheter C up through aortic arch AR. When delivery catheter C is positioned as desired within the patient's vasculature, wire W may be distally translated through delivery catheter C to push device 180 therefrom. As device 180 is deployed from delivery catheter C, tube 181 automatically radially expands to its expanded state. In the expanded state, tube 181 contacts the wall of aortic arch AR to frictionally secure device 180 therein. Device 180 may be positioned in aortic arch AR with distal end 183 positioned closer to ascending aorta AA, upstream with respect to one or more ostia leading to arterial branches B, LC, and/or LS, and proximal end 182 positioned closer to descending aorta DA. Instruments T, such as a valve delivery catheter, may be inserted and translated through the hollow interior 184 of tube 181 and through opening 187 in filter 186. As blood flows through the aorta in the direction of arrow F, filter 186 inhibits the passage of emboli both into one or more of arterial branches B, LC, and/or LS, and downstream of device 180. Once the desired procedure has been completed, device 180 may be retrieved by pulling wire W back through delivery catheter C, which forces the device to its compressed state and repositions it within delivery catheter C for removal from the patient.

Figure 10:
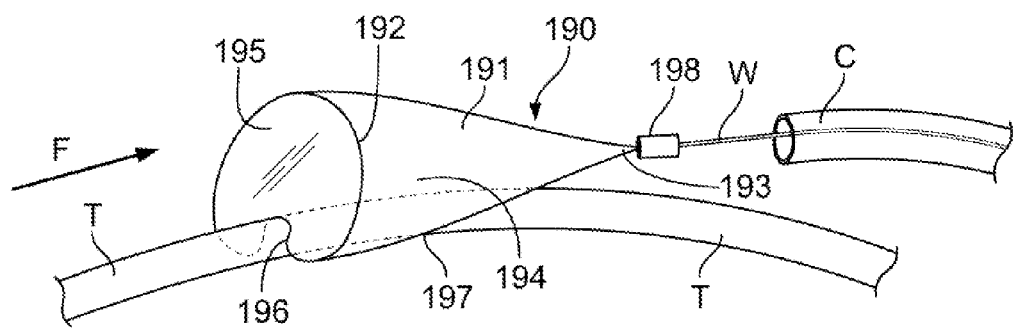
FIG. 10 is a perspective view of another embodiment of an embolic protection device.

Yet another embodiment of embolic protection device, device 190 shown in FIG. 10, is substantially similar to device 180 described above with the exception that device 190 includes a tube 191 having a substantially conical configuration. As with the other embodiments, device 190 may be transitionable between a collapsed condition for insertion into delivery catheter C, and an expanded condition, and preferably is formed from a nickel titanium alloy or other shape memory material that may be coated with a substance having anti-thrombogenic properties. Tube 191 has a distal end 192 and proximal end 193 and hollow interior 194 within tube 191. Tube 191 may be formed from the same materials discussed above with respect to tube 181 of device 180. The diameter of tube 191 at distal end 192 preferably is greater than the diameter of aortic arch AR so that, upon deployment of device 190, the distal end expands into secure frictional engagement with aortic arch AR to hold device 190 in place against blood flow.

Filter 195, which may be substantially similar to filter 186, may be disposed in and may substantially close distal end 192 of tube 191. As with filter 186, filter 195 may include aperture 196 for the reception of instrument T therethrough. Aperture 197 formed in the sidewall of tube 191 leads to hollow interior 194, and is configured and adapted to receive instrument T therethrough. One such instrument T may be preloaded within device 190 or may be placed within device 190 after its deployment so that instrument T passes through aperture 197, hollow interior 194, and opening 196 formed within filter 195. An edge of tube 191 at proximal end 193 may be crimped within crimp tube 198. Crimp tube 198 may couple tube 191 to wire W.

Deployment and retrieval of device 190 is substantially similar to that described above with respect to device 180. When deployed within aortic arch AR, distal end 192 of device 190 may be positioned upstream of an ostium leading to one of aortic branches B, LC, or LS. Filter 195 inhibits the passage of emboli through aortic arch AR. The cone-like configuration of tube 191 may minimize contact between tube 191 and the wall of the aortic arch, which may be advantageous if the wall of the aorta is fragile. In addition, by minimizing contact between tube 191 and the wall of aortic arch AR, distortion of the shape of the tube that might occur if such contact were to take place may be minimized.

Figure 11:
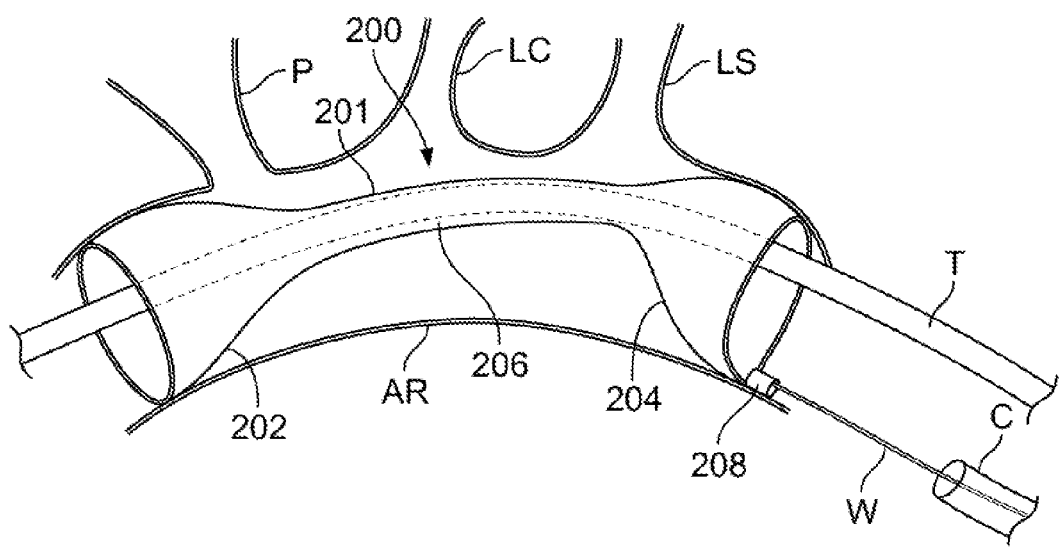
FIG. 11 is a diagrammatic view of yet another embodiment of an embolic protection device disposed within a patient's vascular system.

In a still further embodiment, embolic protection device 200 is shown in FIG. 11. Device 200 includes tube 201 that has first section 202, second section 204, and middle section 206 disposed therebetween. Tube 201 may define an hourglass shape such that first section 202 and second section 204 have relatively large diameters that taper downwardly or narrow as they approach middle section 206. The interior of tube 201 may be hollow such that instrument T may be translated through first section 202, middle section 206, and second section 204. Tube 201 of device 200 may be formed from a braided mesh-like material having shape memory properties, such as those exhibited by a nickel titanium alloy, such that the device may be transitionable between a compressed state and an expanded state. As with the other devices described herein, tube 201 and the other components of device 200 may be coated with a substance having anti-thrombogenic properties. Blood may flow through the mesh-like material of tube 201, while emboli of a predetermined size are deflected and/or captured. An end of one of first section 202 or second section 204 may be contained within crimp tube 208, which may inhibit the braided material of device 200 from unraveling. Wire W may be coupled to crimp tube 208 to facilitate deployment and/or retrieval of device 200 through delivery catheter C.

Device 200 may be deployed within a patient's vasculature using the same percutaneous delivery approaches described above with respect to the other embodiments. For example, device 200 may be delivered via a transfemoral delivery approach in which the device is loaded into delivery catheter C in a compressed condition so that it can fit within delivery catheter C. In particular, device 200 may compress in a radial direction such that its width becomes narrower. In that regard, the axial length of device 200 may correspondingly increase. Once delivery catheter C has been positioned at or near the desired location in the patient's vasculature, device 200 may be deployed by pushing wire W out from the delivery catheter, whereupon it will expand to its normal expanded state (as shown in FIG. 11) from a compressed state in which the diameter of tube 201 has been reduced to fit within delivery catheter C.

In the deployed condition, shown in FIG. 11, device 200 is positioned within aortic arch AR such that instruments T may be translated through tube 201. The tapered middle section 206 spaces instruments T away from the wall of aortic arch AR such that forces applied by instruments T upon the wall of aortic arch AR are minimized, and the interaction between middle section 206 of tube 201 and aortic arch AR is minimized. First section 202 and second section 204 may frictionally engage the wall of aortic arch AR, thereby minimizing the flow of blood between device 200 and the wall of the aortic arch. Since middle section 206 has a narrowed diameter relative to that of first section 202 and second section 204, middle section 206 may be isolated from the wall of aortic arch AR such that the openings between the braided material forming middle section 206 are substantially unaffected by interaction with aortic arch AR. Device 200 may remain deployed throughout the primary procedure. After completing the primary procedure, device 200 may be retrieved by pulling wire W back into delivery catheter C, which causes device 200 to be compressed within the delivery catheter such that it can be removed from the patient as delivery catheter C is withdrawn. Emboli may be trapped within the interstices between the braided material forming tube 201. Additionally, a filter material (not shown) may line tube 201 such that emboli coming in contact with the filter material may be trapped therein.

Figure 12A:
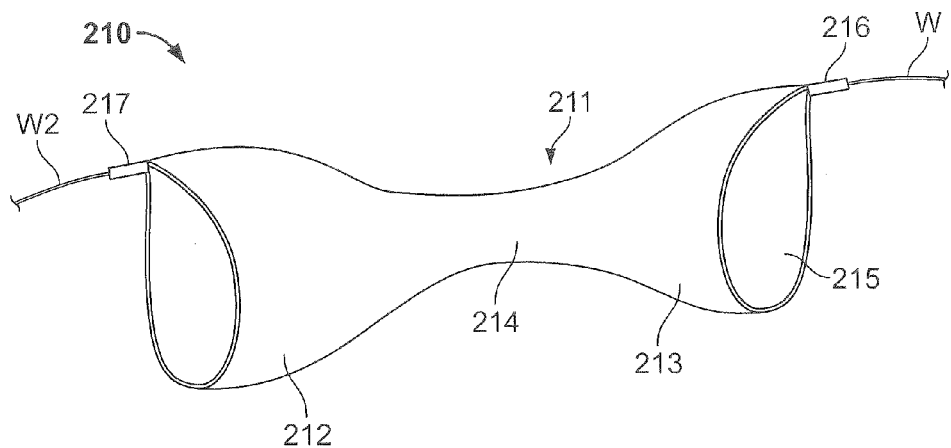
FIG. 12A is a perspective view of yet another embodiment of an embolic protection device shown in a first condition.
Figure 12B:
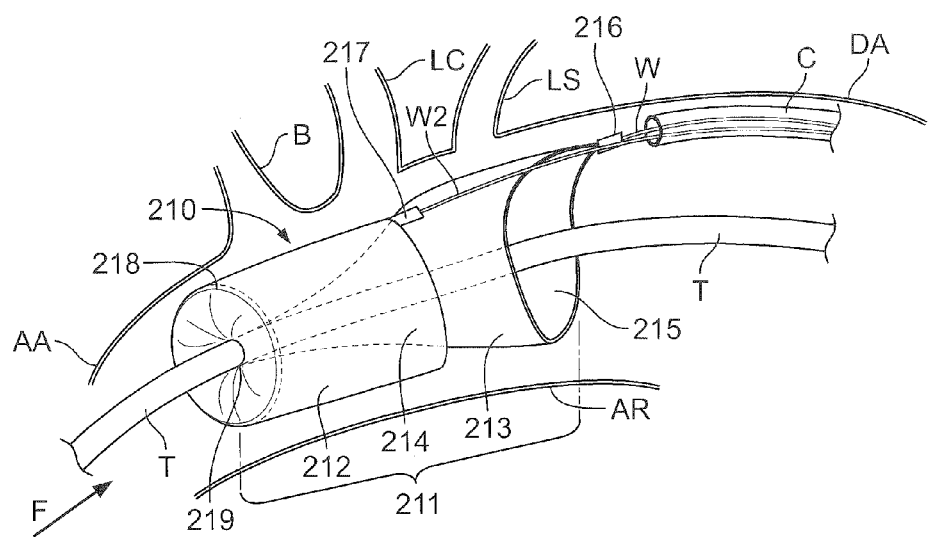
FIG. 12B is a diagrammatic view of the embolic protection device of FIG. 12A.

Yet another embodiment of embolic protection is shown in FIGS. 12A and 12B. Device 210 includes tube 211, which may include distal portion 212, proximal portion 213, and intermediate portion 214 disposed between distal portion 212 and proximal portion 213. Device 210 may be formed from the same materials described above in connection with device 200. That is, tube 211 may be formed from a braided or mesh-like material or from a porous foam through which blood may flow while emboli of a predetermined size are deflected and/or captured, and may be coated with a substance having anti-thrombogenic properties. The material forming tube 211 may have shape memory properties, such as exhibited by a nickel titanium alloy or a porous elastic foam, such that tube 211 is transitionable from a normally expanded state to a compressed state in which it is positionable within delivery catheter C. Tube 211 may have somewhat of an hour-glass configuration with a relatively large diameter at distal portion 212 and proximal portion 213, and a relatively small diameter in intermediate section 214. The diameters of distal portion 212 and proximal portion 213 remain substantially constant for a predetermined length of the tube, as does the diameter of intermediate section 214. The diameter of tube 211 gradually tapers downward from distal portion 212 and proximal portion 213 toward intermediate section 214. Tube 211 includes a hollow interior 215. Crimp tube 216 may contain a proximal end of tube 211, and may couple tube 211 to wire W. Another crimp tube 217 may contain a distal end of tube 211, and may couple tube 211 to wire W2.

As shown in FIG. 12B, distal portion 212 of tube 211 may be everted and rolled back over intermediate section 214. As a result, tube 211 in this folded condition has a substantially constant diameter at its proximal end corresponding to proximal portion 213 of the unfolded tube. When in this folded condition, the distal end of tube 211 is folded over upon and covers the region of intermediate section 214 that tapers to a smaller diameter from the proximal end of tube 211 toward the distal end of tube 211. When in this folded condition, the substantially constant diameter of distal portion 212 of tube 211 surrounds the smaller diameter of intermediate section 214. Thus, by rolling distal portion 212 of tube 211 back over the intermediate section 214, a relatively small diameter opening 219 extending through tube 211 is formed. Proximal portion 213 of tube 211 may have a hollow interior 215 that tapers inwardly along its length from the substantially constant diameter portion to the relatively small diameter opening 219 at which it joins intermediate section 214. The diameter of opening 219 is sized so as to receive therethrough instruments T for performing the desired procedure.

Filter 218 may be operatively coupled to the distal end of tube 211. For example, filter 218 may be stitched within a portion of distal portion 212 so that when distal portion 212 is folded filter 218 is at the distal end of device 210, as shown in FIG. 12B. Filter 218 may include an opening (not shown) that is aligned with opening 219 through tube 211. Filter 218 may be disposed within tube 211 to protect filter 218 from damage. Filter 218 may be formed from a material that will allow blood to flow therethrough while inhibiting the passage of emboli as the blood flows through the aorta in the direction of arrow F. For example, filter 218 may be formed from a polymer, such as a polyurethane foam, a sufficiently porous fabric material, or other similar types of materials capable of providing a filtering function. A filter material may be operatively coupled to or integrated into the mesh-like material forming tube 211 along substantially the entire length of tube 211 or along substantially the entire length of distal portion 212 of tube 211.

Deployment of device 210 may be achieved by compressing the device in the folded condition and loading it into delivery catheter C. In the compressed condition, the width or radial dimension of device 210 is narrower than in the expanded condition. Delivery catheter C may be delivered via a transfemoral approach and maneuvered toward aortic arch AR. Once delivery catheter C is at a desired position in the patient's vasculature, wire W may be distally translated through delivery catheter C. As wire W moves distally, device 210 is pushed out from delivery catheter C and expands to its expanded configuration, as shown in FIG. 12A, to radially contact the wall of aortic arch AR. The distal end of device 210 may be positioned upstream of one or more ostia leading to arterial branches B, LC, and/or LS to minimize/prevent the passage of emboli therethrough.

After deploying device 210 into aortic arch AR, wire W2 may be proximally drawn into catheter C to cause distal portion 212 to fold proximally over intermediate section 214. Device 210 may be biased toward a expanded condition and may automatically transition to its expanded condition upon deployment. With device 210 expanded so as to fill the cross-section of aortic arch AR, elongated instrument T, such as a valve delivery catheter, may be guided through hollow interior 215 of proximal portion 213 and through opening 219 so as to reach the target site. The tapered shape of proximal portion 213 may facilitate a desired spacing of such instrumentation from the walls of the aortic arch. At this juncture, any blood flowing in the direction of arrow F, including during a procedure performed upstream of device 210, will pass through the mesh-like material of distal portion 212 and through the mesh-like material of proximal portion 213, then out from device 210 through hollow interior 215 at the proximal end of device 210. Emboli may be trapped by the mesh-like material of distal portion 212 or by a filter disposed on or within distal portion 212, such as filter 218. Once the subsequent procedure has been completed, device 210 may be retrieved by translating wire W and/or wire W2 proximally to pull the device into delivery catheter C. As device 210 is withdrawn into delivery catheter C, tube 211 may be forced into a compressed condition as it engages the wall of catheter C, in which it has a reduced diameter so that tube 211 may be loaded into catheter C. Once retrieved into catheter C, device 210 along with any emboli captured therein may be removed from the patient as catheter C is withdrawn from the patient.

Figure 13:
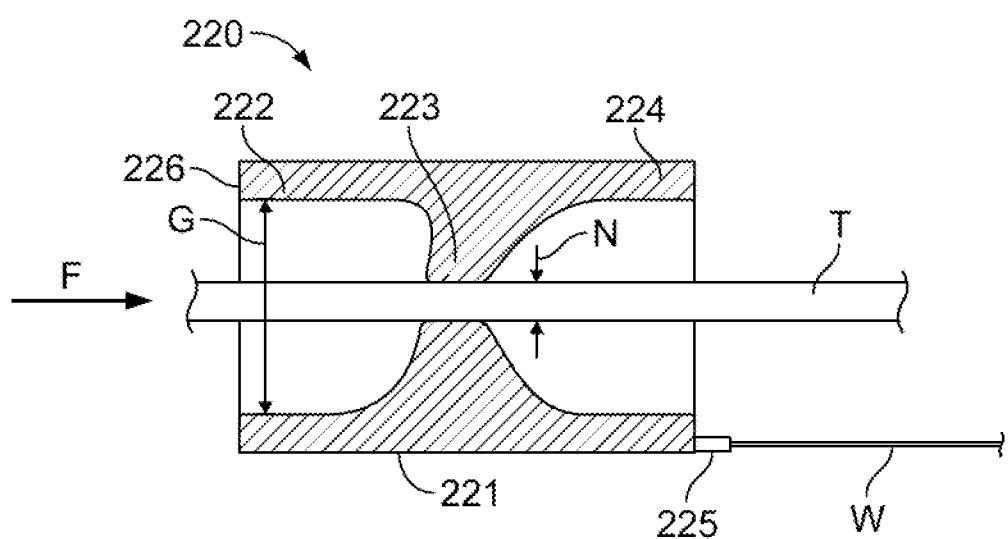
FIG. 13 is a side cross-sectional view of a further embodiment of an embolic protection device.

In a still further embodiment, shown in FIG. 13, embolic protection device 220 includes tube 221 having distal section 222 having inner diameter G, middle section 223 configured to snuggly receive instrument T, and proximal section 224 which may have a diameter that tapers toward middle section 223. Proximal section 224 may have an inner diameter that narrows in the fully expanded condition from its free end toward inner diameter N of middle section 223. Inner diameter N of middle section 223 may approximate the diameter of instrument T. The tapered shape of proximal section 224 may facilitate guiding elongated instrument T into and through middle section 223. As with the previously described embodiments, device 220 may be transitionable between a collapsed condition for insertion into a delivery catheter, and an expanded condition, and preferably is formed from a nickel titanium alloy or other shape memory material. Also, as with the previously described embodiments, device 220 may be coated by a substance having anti-thrombogenic properties. Distal section 222 and proximal section 224 of tube 221 may have a substantially uniform inner diameter G in the fully expanded condition. When fully expanded, device 220 preferably has an outer diameter that is larger than the diameter of the aorta so that, upon deployment, the device may securely engage the wall of the aorta to hold the device in place. Crimp tube 225 may be crimped to the material forming tube 221 at the proximal end thereof and may couple the tube to wire W.

The delivery, deployment and retrieval of device 220 may be accomplished in the manner described above in connection with the other embodiments. In the deployed condition, distal end 226 of tube 221 may be positioned upstream relative to one or more of arterial branches B, LC, and LS. As such, blood flowing in direction F passes through the mesh of middle section 223 and through the mesh of tube 221. The wall of tube 221 deflects emboli larger than a predetermined size from entering arterial branches B, LC, and/or LS, and middle section 223 prevents emboli larger than a predetermined size from passing through device 220 toward descending aorta DA. Accordingly, emboli present in the blood may collect within distal section 222. Device 220 therefore inhibits passage of emboli both through aortic arch AR, as well as into arterial branches B, LC, and/or LS.

Figure 14A:
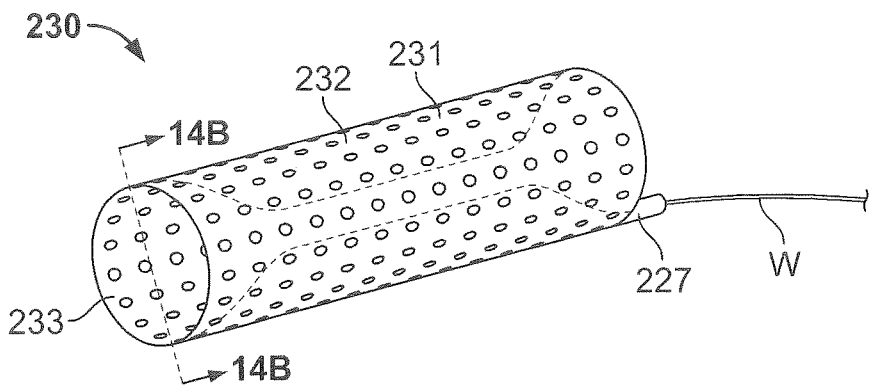
FIG. 14A is a perspective view of a still further embodiment of an embolic protection device.
Figure 14B:
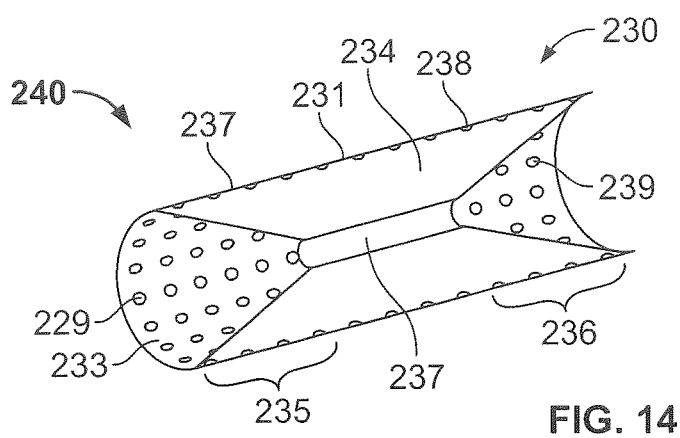
FIG. 14B is a perspective cross-sectional view of the embolic protection device taken along section line 14B-14B of FIG. 14A.

Yet another embodiment of embolic protection device 230 is shown in FIGS. 14A and 14B. Device 230 includes tube 231 formed from a porous foam or from a braided, mesh-like material. Tube 231 may have shape memory properties, such as exhibited by a nickel titanium alloy or a porous elastic foam, and may be biased toward an expanded state such that, after being compressed, the material will transition back toward the expanded state. As with the previously described embodiments, the components of device 230 may be coated with a substance having anti-thrombogenic properties. Tube 231 may have outer surface 232 and inner surface 233, and hollow space 234 may be disposed between outer surface 232 and inner surface 233. Inner surface 233 of device 230 may include first section 235 and second section 236 that taper toward a relatively narrow lumen 237 through which an instrument may be inserted. Narrow lumen 237 is positioned between first section 235 and second section 236. Inner surface 233 of first section 235 of tube 231 may include a plurality of pores 229. Outer surface 232 of tube 231 may include a plurality of pores 238, and inner surface 233 of tube 231 may include a plurality of pores 239 at the downstream end of tube 231. Device 230 may be placed within the aortic arch such that blood flows from first section 235 toward second section 236. Preferably, emboli within the flowing blood may enter hollow space 234 but are inhibited from exiting. In that regard, pores 229 at the upstream end of device 230 may be larger than pores 239 at the downstream end of device 230. In addition, pores 238 which permit blood to flow to the arterial branches may be smaller than pores 229 to inhibit passage of emboli to those branches. Thus, emboli within the flowing blood may pass through pores 229 into hollow space 234 and may be inhibited from exiting hollow space 234 through pores 238 and/or 239. Lumen 237 may be substantially closed in the absence of an instrument inserted therein, and the diameter of lumen 237 may approximate that of the instrument when the instrument is inserted therein so that emboli within the flowing blood may be inhibited from entering lumen 237 when device 230 is deployed and are instead directed into hollow space 234, as described above. One end of device 230 may be coupled to a crimp tube 227 to contain the loose ends of braided material therein, and to facilitate coupling device 230 to wire W.

Device 230 may be deployed via the percutaneous delivery approaches described above with reference to the other embolic protection device embodiments. Device 230 may be loaded within a delivery catheter, which may be maneuvered toward the aortic arch AR. Once at a desired position within the patient's vasculature, device 230 may be deployed by pushing wire W out from the delivery catheter. As device 230 is deployed, tube 231 may automatically expand and frictionally contact the wall of aortic arch AR. In the deployed condition, one or more of the ostia leading to arterial branches B, LC, and LS are shielded by device 230, thus minimizing the potential of emboli passing into those arterial branches. When tube 231 is placed in apposition with the wall of aortic arch AR, emboli larger than a predetermined size that are within blood flowing through the aortic arch may be directed into hollow space 234, as described above, and may be trapped therein. Device 230 may remain deployed throughout the course of the primary procedure, such as a TAVI procedure. Once the primary procedure has been completed, device 230 may be retrieved by pulling wire W back through the delivery catheter.

Figure 15:
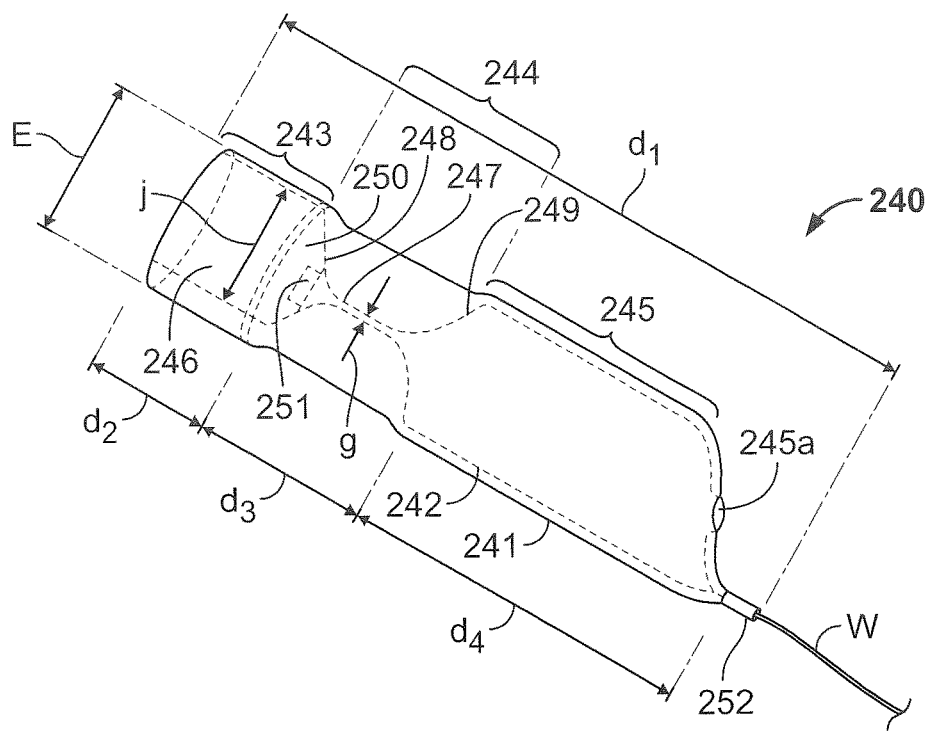
FIG. 15 is a perspective view of a still further embodiment of an embolic protection device.

In still a further embodiment, embolic protection device 240 is shown in FIG. 15. Embolic protection device 240 may be formed from a braided or mesh-like material or from a porous foam through which blood may flow while emboli of a predetermined size are deflected and/or captured before they can enter branches B, LC, and/or LS of aortic arch AR. The material forming device 240 may exhibit shape memory properties, such as those exhibited by a nickel titanium alloy or a porous elastic foam, such that the device is compressible to a smaller size that may be translated through a delivery catheter. As with the previously described embodiments, the components of device 240 may be coated with a substance having anti-thrombogenic properties.

Device 240 may include a tubular structure having outer layer 241 and inner layer 242. Inner layer 242 and outer layer 241 may be formed by folding a tube into itself so that the tube inverts, thereby forming the outer and inner layers. Outer layer 241 may have first diameter E and a length d1, e.g., about 8-12 cm, in an expanded condition. Inner layer 242 may be divided into first section 243, second section 244, and third section 245. First section 243 and third section 245 of inner layer 242 may have a diameter j that approximates the diameter E of outer layer 241. First section 243 may have a generally cylindrical opening 246. Second section 244 may be disposed between first section 243 and third section 245, and may include a longitudinally extending lumen 247, which has second diameter g, for the reception of an elongated instrument therethrough. Third section 245 may include an aperture 245a for the reception of the instrument therethrough. A surgical instrument is insertable through first section 243, second section 244, and third section 245. Lumen 247 may be transitionable between an expanded condition and a compressed condition so that when an instrument is inserted therethrough, lumen 247 may approximate the diameter of the instrument. At second section 244, inner layer 242 may be substantially evenly spaced from outer layer 241. Thus, when an instrument is inserted through second section 244, it may be spaced by substantially the same radial distance from outer layer 241. First section 243 may have length d2, second section 244 may have length d3, and third section 245 may have length d4, in which length d2 is less than the length d3, which is less than length d4. For example, d2 may be about 1-2 cm, d3 may be about 2-3 cm, and d4 may be about 5-7 cm.

The narrowed, second diameter g of second section 244 is dimensioned such that the second section 244 may conform to and approximate the diameter of an elongated instrument inserted therethrough. First tapered portion 248 may be positioned between first section 243 and second section 244. Second tapered portion 249 may be positioned between second section 244 and third section 245. Tapered portions 248 and 249 may facilitate insertion of an elongated instrument through the interior of second section 244. Advantageously, the positioning of second section 244 at a distance away from outer layer 241 may minimize the potential that an elongated instrument translated through device 240 may damage the wall of aortic arch AR.

Filter 250 may be disposed or secured within tapered section 248 between first section 243 and second section 244. Filter 250 may facilitate capture and/or deflection of emboli within blood flowing through into device 240 from first section 243. Filter 250 may be a relatively thin membrane having a disk like configuration formed from a material capable of performing a filtering function, such as a porous polymer. Filter 250 may be transitionable between a normally expanded state and a compressed state, and may include a throughhole 251 to facilitate insertion of an elongated instrument therethrough. Crimp tube 252 may contain the loose ends of the material of third section 245 therein, and may be operatively coupled to wire W.

Device 240 may be deployed via any suitable percutaneous delivery approach as may be employed by the devices described hereinabove. For example, device 240 may be delivered via a transfemoral approach in which the device is loaded into a delivery catheter that is then maneuvered up to aortic arch AR. Device 240 is deployed from the delivery catheter by pushing wire W through the delivery catheter. In the deployed condition, device 240 may be positioned within aortic arch AR so as to shield one or more of the ostia leading to arterial branches B, LC, and LS of aorta A, thereby inhibiting emboli from entering these arterial branches. Preferably, first section 243 may be placed upstream relative to the brachiocephalic artery B to minimize the flow of emboli into each of the arterial branches B, LC, and LS. Device 240 may be left in such a position throughout the performance of a primary procedure, such as a TAVI procedure. Once the primary procedure has been performed, device 240 may be retrieved by pulling wire W back into the delivery catheter.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that any individual features described in connection with any embodiment may be shared with others of the described embodiments. The alternative embodiments presented hereinabove are not mutually exclusive, but may be implemented in various combinations to achieve unique advantages. As these and other variations and combinations of the features discussed above can be utilized without departing from the invention as defined by the claims, the foregoing description of the embodiments should be taken by way of illustration rather than by way of limitation.

By way of illustration only, the embolic protection devices described herein may include a tubular sheet having a first end and a second end; and a delivery catheter, the first end of the tubular sheet being fixedly connected to the delivery catheter, and the second end of the tubular sheet being translatable through the delivery catheter; and/or translation of the second end of the tubular sheet into the delivery catheter progressively may invert the tubular sheet to retract the tubular sheet into the delivery catheter; and/or translation of the second end of the tubular sheet out from the delivery catheter progressively everts the tubular sheet to deploy the tubular sheet from the delivery catheter; and/or may include an elongated delivery rod disposed for sliding movement within the delivery catheter, the second end of the tubular sheet may be operatively coupled to the delivery rod so that sliding movement of the delivery rod in a proximal direction retracts the tubular sheet into the delivery catheter and sliding movement of the delivery rod in a distal direction deploys the tubular sheet from the delivery catheter.

The embolic protection devices may further include an elongated tubular body having a proximal section, a distal section, and an intermediate section between the proximal section and the distal section, the intermediate section having a first diameter and the proximal and distal sections each having a diameter that is greater than the first diameter, the elongated tubular body being transitionable between an unfolded configuration in which the intermediate section is positioned between the proximal and distal sections and a folded configuration in which the distal section is inverted over the intermediate section; and/or including a filter material disposed in the distal section.

The embolic protection devices may also include a tube formed from a compressible material, the tube having a first end, a second end, and a diameter; and a wire operatively coupling the first end and the second end of the tube, the wire being translatable relative to the tube to cause a corresponding movement of the first end of the tube relative to the second end of the tube and a corresponding change in the diameter of the tube.

The embolic protection devices may also include a tube transitionable between a compressed condition and an expanded condition and including a first section having a first diameter and a second section having a second diameter, the second diameter being smaller than the first diameter, the first section including a first lumen through which the second section is translatable, the second section including a second lumen through which an elongated instrument is insertable; and/or the first section may have a hollow interior; and/or may include at least one opening positioned between the first section and the second section, the at least one opening may be sized to permit passage of emboli of a predetermined size into the hollow interior.

The embolic protection devices may further include a tubular member having an outer layer and an inner layer, the inner layer having a first section with a first diameter, a second section with a second diameter, and an intermediate section positioned between the first section and the second section, the intermediate section having a diameter smaller than diameters of the first and second sections, wherein a lumen extends continuously through the first section, the second section, and the intermediate section, the lumen being configured to receive an elongated instrument therethrough; and/or a filter may be disposed within the first section; and/or the elongated instrument may have a diameter, and the diameter of the intermediate section may be about equal to the diameter of the instrument; and/or the tubular member may be operatively coupled to a wire; and/or the tubular member may be coated with an anti-thrombogenic substance; and/or tubular member may be formed from a braided material; and/or the tubular member may have an upstream end, a downstream end, and a plurality of openings, the openings at the upstream end being larger than the openings at the downstream end.

The embolic protection devices may also include an elongated tubular body having a longitudinal axis, a first section, a second section, and a third section, the body being configured to transition between an expanded state and a compressed state, and being biased toward the expanded state, the second section being disposed between the first section and the third section, the second section being relatively narrower than the first section and the third section in the expanded state; and a lumen extending through the body along the longitudinal axis, the lumen being sized to receive an elongated instrument therethrough, the elongated instrument being radially spaced from outer surfaces of the first section and the third section when the elongated instrument is positioned within the lumen; and/or the tubular body may be formed form a braided alloy; and/or may include a filter material lining the tubular body.

The invention claimed is:

1. An embolic protection device, comprising:
a tubular member having an upstream end, a downstream end, an outer layer and an inner layer, the outer layer having a substantially constant diameter from the upstream end to the downstream end and the inner layer having a first section, a second section, and an intermediate section positioned between the first section and the second section, the intermediate section of the inner layer having a single lumen with an intermediate diameter smaller than the substantially constant diameter, the first section of the inner layer being connected to the outer layer at the upstream end of the tubular member and having a diameter that decreases from the substantially constant diameter at the upstream end of the tubular member to the intermediate diameter of the single lumen at one end of the intermediate section and the second section of the inner layer being connected to the outer layer at the downstream end of the tubular member and having a diameter that decreases from the substantially constant diameter at the downstream end of the tubular member to the intermediate diameter of the single lumen at another end of the intermediate section so that the inner layer is spaced apart from the outer layer in the first section, the second section and the intermediate section, wherein the inner layer defines a continuous lumen extending through the first section, the second section, and the intermediate section, the single lumen being a portion of the continuous lumen, the continuous lumen being configured to receive an elongated instrument therethrough, the inner layer having a plurality of inner pores, the inner pores at the upstream end of the inner layer being larger than the inner pores at the downstream end of the inner layer, and the outer layer including a plurality of outer pores that are smaller than the inner pores at the upstream end of the inner layer.

2. The embolic protection device of claim 1, wherein a filter is disposed within the first section.

3. The embolic protection device of claim 1, wherein the tubular member is operatively coupled to a wire.

4. The embolic protection device of claim 1, wherein the tubular member is coated with an anti-thrombogenic substance.

5. The embolic protection device of claim 1, wherein the tubular member is formed from a braided material.

6. The embolic protection device of claim 1, wherein the tubular member is formed from a porous foam.

7. An embolic protection device, comprising:
an elongated tubular body having an upstream end, a downstream end, a longitudinal axis, a first section, a second section, and a third section, the tubular body being configured to transition between an expanded state and a compressed state, and being biased toward the expanded state, the second section being disposed between the first section and the third section, the first section, the second section and the third section each having an inner surface with a diameter and an outer surface with a diameter, wherein the inner surface diameter of the second section is narrower than the inner surface diameters of the first section and the third section in the expanded state, wherein the outer surface diameters of the first section, the second section and the third section in the expanded state are about equal to one another and are greater than the inner surface diameters of the first section, the second section and the third section in the expanded state, the inner surface of the first section having one end connected to the outer surface of the first section at the upstream end of the tubular body and another end connected to the inner surface of the second section at an upstream end of the second section, the inner surface of the first section including a plurality of first pores, and the inner surface of the third section having one end connected to the outer surface of the third section at the downstream end of the tubular body and another end connected to the inner surface of the second section at a downstream end of the second section, the inner surface of the third section including a plurality of second pores that are smaller than the first pores, and the outer surfaces of the first section, the second section and the third section including a plurality of third pores that are smaller than the first pores,
wherein the inner surface of the second section forms a single lumen extending through the second section, a longitudinal axis of the lumen being coincident with the longitudinal axis of the tubular body, the lumen being sized to receive an elongated instrument therethrough so that the elongated instrument is radially spaced from the outer surface of the first section and the outer surface of the third section when the elongated instrument is positioned within the lumen.

8. The embolic protection device of claim 7, wherein the tubular body is formed from a braided alloy.

9. The embolic protection device of claim 7 further comprising a filter material lining the tubular body.

10. An embolic protection device, comprising:
a tubular member having an upstream end, a downstream end, an outer layer and an inner layer, the outer layer having a substantially constant diameter from the upstream end to the downstream end and the inner layer having a first section with a first diameter, a second section with a second diameter, and an intermediate section positioned between the first section and the second section, the intermediate section having a third diameter smaller than the first and second diameters, the first diameter, the second diameter and the third diameter each being less than the constant diameter so that the inner layer is spaced apart from the outer layer in the first section, the second section and the intermediate section, the first section of the inner layer including a plurality of first pores and being connected to the outer layer at the upstream end of the tubular member, the second section of the inner layer including a plurality of second pores smaller than the first pores and being connected to the outer layer at the downstream end of the tubular member, and the outer layer including a plurality of third pores smaller than the first pores, wherein a lumen extends continuously through the first section, the second section, and the intermediate section, the lumen being configured to receive an elongated instrument therethrough.

11. An embolic protection device, comprising:

an elongated tubular body having an upstream end, a downstream end, a longitudinal axis, a first section, a second section, and a third section, the tubular body being configured to transition between an expanded state and a compressed state, and being biased toward the expanded state, the second section being disposed between the first section and the third section, the first section, the second section and the third section each having an inner surface with a diameter and an outer surface with a diameter, wherein the inner surface diameter of the second section is narrower than the inner surface diameters of the first section and the third section in the expanded state, wherein the outer surface diameters of the first section, the second section and the third section in the expanded state are about equal to one another and are greater than the inner surface diameters of the first section, the second section and the third section in the expanded state, the inner surface of the first section including a plurality of first pores and the inner surface of the first section being connected to the outer surface of the first section at the upstream end of the tubular body, the inner surface of the third section including a plurality of second pores smaller than the first pores and the inner surface of the third section being connected to the outer surface of the third section at the downstream end of the tubular body, and the outer surfaces including a plurality of third pores smaller than the first pores; and a lumen extending through the tubular body along the longitudinal axis, wherein the lumen is sized to receive an elongated instrument therethrough, and the elongated instrument is radially spaced from the outer surface of the first section and the outer surface of the third section when the elongated instrument is positioned within the lumen.

* * * * *